United States Patent
Li et al.

(10) Patent No.: US 9,572,876 B2
(45) Date of Patent: Feb. 21, 2017

(54) PARAMYXOVIRUS IMMUNOGENS AND RELATED MATERIALS AND METHODS

(75) Inventors: Jianrong Li, Dublin, OH (US); Yu Zhang, Columbus, OH (US); Rongzhang Wang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 103 days.

(21) Appl. No.: 14/124,501

(22) PCT Filed: Jun. 11, 2012

(86) PCT No.: PCT/US2012/041878
§ 371 (c)(1),
(2), (4) Date: Feb. 14, 2014

(87) PCT Pub. No.: WO2012/170997
PCT Pub. Date: Dec. 13, 2012

(65) Prior Publication Data
US 2015/0079117 A1    Mar. 19, 2015

Related U.S. Application Data

(60) Provisional application No. 61/495,119, filed on Jun. 9, 2011.

(51) Int. Cl.
| | | |
|---|---|---|
| *C12N 7/00* | (2006.01) | |
| *C12N 7/04* | (2006.01) | |
| *A61K 39/155* | (2006.01) | |
| *A61K 39/12* | (2006.01) | |
| *A61K 38/45* | (2006.01) | |
| *A61K 39/00* | (2006.01) | |

(52) U.S. Cl.
CPC ............ *A61K 39/155* (2013.01); *A61K 38/45* (2013.01); *A61K 39/12* (2013.01); *C12N 7/00* (2013.01); *A61K 2039/5254* (2013.01); *A61K 2039/542* (2013.01); *A61K 2039/543* (2013.01); *C12N 2760/18334* (2013.01); *C12N 2760/18362* (2013.01); *C12N 2760/18534* (2013.01); *C12N 2760/18562* (2013.01); *C12N 2760/18634* (2013.01); *C12N 2760/18662* (2013.01); *C12Y 207/07006* (2013.01)

(58) Field of Classification Search
None
See application file for complete search history.

(56) References Cited

U.S. PATENT DOCUMENTS

2009/0169580 A1 * 7/2009 Whelan et al. ............ 424/199.1

OTHER PUBLICATIONS

PCT International Search Report and Written Opinion, Application No. PCT/US202012/041,878, dated Sep. 5, 2012.
Li, J., et al., "A Conserved Motif in Region V of the Large Polymerase Proteins of Nonsegmented Negative-Sense RNA Viruses that is Essential for mRNA Capping," Journal of Virology, epub. Nov. 14, 2007, 82(2):775.

* cited by examiner

*Primary Examiner* — Stacy B Chen
(74) *Attorney, Agent, or Firm* — MacMillan, Sobanski & Todd, LLC

(57) ABSTRACT

The present invention includes methyltransferase (MTase)-defective recombinant viruses as live vaccine candidates for human metapneumovirus (hMPV), human respiratory syncytial virus (hRSV), and human parainfluenza virus type 3 (PIV3). Here the inventors provide the technical description for generating MTase-defective paramyxoviruses useful as immunogens, as well as related materials and methods.

Figure 1:
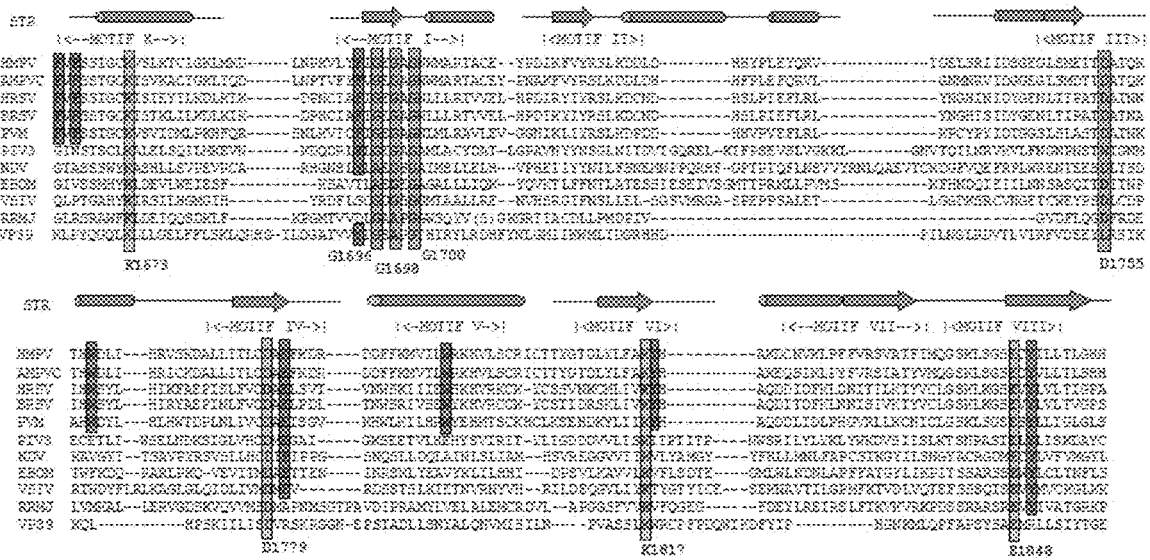

9 Claims, 11 Drawing Sheets
(8 of 11 Drawing Sheet(s) Filed in Color)

| Virus | MTase catalytic site | MTase SAM binding site |
|---|---|---|
| human metapneumovirus (hMPV) | rhMPV-K1673A, rhMPV-D1779A, rhMPV-K1817A, rhMPV-E1848A, and rhMPV-E1848Q. Mutant hMPV carrying two or three amino acid substitutions in catalytic site were also recovered. | rhMPV-G1696A, rhMPV-G1698A, rhMPV-G1700A, and rhMPV-D1755A. Mutant hMPV carrying two or three amino acid substitutions in SAM binding site were also recovered. |
| human respiratory syncytial virus (hRSV) | rRSV-K1831A, rRSV-D1936A, rRSV-K1973A, rRSV-E2004A Mutant RSV carrying two or three amino acid substitutions in catalytic site were also recovered. | rRSV-G1853A, rRSV-G1855A, rRSV-G1857A, and rRSV-D1912A. Mutant hRSV carrying two or three amino acid substitutions in SAM binding site were also recovered. |
| human parainfluenza virus type 3 (PIV3) | rPIV3-K1786A, rPIV3-D1905A, rPIV3-K1941A, rPIV3-E1978A Mutant PIV3 carrying two or three amino acid substitutions in catalytic site were also recovered. | rPIV3-G1808A, rPIV3-G1810A, rPIV3-G1812A, and rPIV3-W1880A. Mutant PIV carrying two or three amino acid substitutions in SAM binding site were also recovered. |

| Virus | Dose (Log10 PFU/hamster) | Number of hamsters | Days post-challenge | % of animals with detectable virus in lungs | Lung histology (severity of damage) |
|---|---|---|---|---|---|
| DMEM control | 0 | 5 | 4 | 0 | No damage |
| Wild type rhMPV | 6.48 | 5 | 4 | 100 | Moderate to severe |
| Wild type rhMPV | 5.0 | 5 | 4 | 100 | Moderate |
| Wild type rhMPV | 4.0 | 5 | 4 | 100 | Moderate |
| rhMPV-G1696A | 6.48 | 5 | 4 | 100 | Moderate |
| rhMPV-G1696A | 5.0 | 5 | 4 | 100 | Mild |
| rhMPV-G1696A | 4.0 | 5 | 4 | 100 | No to Mild |
| rhMPV-G1700A | 6.48 | 5 | 4 | 80 | Moderate |
| rhMPV-G1700A | 5.0 | 5 | 4 | 80 | Mild |
| rhMPV-G1700A | 4.0 | 5 | 4 | 80 | No to Mild |
| rhMPV-D1755A | 6.48 | 5 | 4 | 100 | Moderate |
| rhMPV-D1755A | 5.0 | 5 | 4 | 100 | Mild |
| rhMPV-D1755A | 4.0 | 5 | 4 | 100 | No to Mild |

Fig.10B

| Virus | Immunization dose (Log10 PFU/hamster) | Number of hamsters | Days post-challenge | Lung histology post-challenge (severity of damage) | Protection rate |
|---|---|---|---|---|---|
| PBS normal control | 0 | 5 | 4 | No damage | / |
| PBS challenge control | 0 | 5 | 4 | Severe damage | 0/5 |
| rhMPV-G1696A | 5.0 | 5 | 4 | No damage | 5/5 |
| rhMPV-G1696A | 4.0 | 5 | 4 | No damage | 5/5 |
| rhMPV-G1700A | 5.0 | 5 | 4 | No damage | 5/5 |
| rhMPV-G1700A | 4.0 | 5 | 4 | No to mild damage | 5/5 |
| rhMPV-D1755A | 5.0 | 5 | 4 | No damage | 5/5 |
| rhMPV-D1755A | 4.0 | 5 | 4 | No to mild damage | 5/5 |

Fig.11

PARAMYXOVIRUS IMMUNOGENS AND RELATED MATERIALS AND METHODS

CROSS REFERENCE TO RELATED APPLICATIONS

This application claims the benefit of PCT application No. PCT/US2012/041878 filed Jun. 11, 2012, which claims priority to U.S. Provisional Patent Application No. 61/495,119 filed Jun. 9, 2011, the disclosure of which is incorporated herein by reference, in its entirety.

STATEMENT REGARDING FEDERALLY SPONSORED RESEARCH

This invention was made with U.S. Government financial support under 60026680, awarded by NIH/NIAID R56 and 60024452 awarded by NIH/NIAID R01. The government may have certain rights in this invention.

REFERENCE TO SEQUENCE LISTING SUBMITTED VIA EFS-WEB

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_53068_SeqListing_OSU-2011-146.txt, created on Jun. 11, 2012 and is 19,469 bytes in size.

TECHNICAL FIELD OF THE INVENTION

The present invention relates to biotechnology, including modified viruses. The invention is in the field of medicine and immunology, including immunogen delivery to living cells and organisms.

BACKGROUND OF THE INVENTION

Paramyxoviruses are the leading causative agents of acute viral respiratory tract infections. Among the paramyxoviruses, human metapneumovirus (hMPV), human respiratory syncytial virus (RSV), and human parainfluenza virus type 3 (hPIV3) account for more than 70% of acute viral respiratory diseases. All of three viruses cause similar clinical signs and symptoms, ranging from mild respiratory problems to sever coughs, bronchiolitis, and pneumonia. All three viruses cause acute respiratory tract disease in individuals of all ages, especially in infants, children, the elderly, and immunocompromised individuals. In the United States, 60% of infants are infected during their first RSV season, and nearly all children will have been infected with the virus by 2-3 years of age. HMPV is a newly discovered human pathogen, first identified in 2001 in The Netherlands. Soon after its discovery, hMPV was recognized as a globally prevalent pathogen. Epidemiological studies suggest that 5 to 15% of all respiratory tract infections in infants and young children are caused by hMPV, a proportion second only to that of RSV. PIV3 is the third causative agent of viral respiratory infection in children and infants. All three pathogens are globally prevalent.

Despite the enormous economic losses and emotional burdens these viruses cause, vaccines and anti-viral drugs are currently not available. For decades, approaches to generate vaccines employing viral proteins or inactivated vaccines have failed either due to a lack of immunogenicity or the potential for causing enhanced pulmonary disease upon natural infection with the same virus.

Vaccination has been the most effective public health strategy to reduce morbidity and mortality associated with viral infections. The increasing clinical significance of RSV, hMPV and PIV3 infections suggest that there is an urgent need for a safe and efficacious vaccine against these viruses, particularly for the populations at high risk such as infants, children, elderly, and immunocompromised individuals. An effective vaccine would not only prevent acute respiratory tract infection caused by these viruses, but also block transmission routes and thus improve human and public health. In the current inventions, the inventors developed a panel of live attenuated vaccines against RSV, hMPV and PIV3.

However, development of vaccine against human paramyxoviruses has met serious challenge. With the exception of the influenza virus, there is no FDA approved vaccine for other viruses that cause acute upper and lower respiratory tract infections in human. Generally, inactivated and live attenuated vaccines are the two most common strategies used in vaccines against infectious diseases. For safety, an inactivated vaccine is preferred. However, development of an inactivated vaccine for the paramyxovirus RSV turned out to be a problem. A formalin-inactivated RSV vaccine developed and tested in the 1960s not only failed to induce a protective immune response in human, but led to an enhanced respiratory disease upon natural infection with RSV. Eighty percent of the vaccinated children were hospitalized following natural RSV infection, and two children died. Enhanced respiratory disease following vaccination with inactivated vaccine has been observed in other paramyxoviruses such as PIV-3, hMPV and measles virus. A recent study showed that cotton rats immunized with inactivated hMPV vaccine were protected against infection, but developed increased lung pathology. These observations suggest that inactivated vaccines are not the primary choices for three paramyxoviruses: hMPV, RSV, and PIV3, all of which cause extensive morbidity and mortality in the same population, infants and children.

In contrast to inactivated vaccines, enhanced lung diseases have not been observed for candidate live attenuated RSV vaccines. Therefore, live attenuated vaccines are the most promising vaccine candidates for hMPV, RSV, and PIV3. However, it has been technically challenging to isolate a virus with low virulence that retains high immunogenicity. In paramyxoviruses, spike proteins (F and G proteins for RSV and hMPV) are major determinants of virulence. Therefore, traditional attenuation strategies have been focused on engineering mutations in these two glycoproteins. However, F and G proteins are also viral immunogenic antigens that are responsible for immune response. As a consequence, mutations in glycoproteins may impair the immunogenicity of the attenuated live vaccine. Therefore, exploration of new attenuation approaches is urgently needed.

This invention develops new attenuated viruses as live vaccine candidates for major human paramyxoviruses including hMPV, RSV and PIV3 by targeting viral mRNA cap methyltransferase (MTase). Paramyxoviruses share a common strategy for replication and gene expression. During RNA synthesis, paramyxoviruses yield capped, methylated, and polyadenylated mRNAs. Methylation of the mRNA directly impacts the stability of mRNA and subsequent translation of viral proteins, which in turn affects viral genome replication, virus assembly, and budding. The large (L) polymerase protein catalyzes the mRNA cap MTases. Recombinant virus defective in MTase can be recovered from cloned full-length viral cDNA by a reverse genetics system. Viruses lacking MTase would likely be attenuated without affecting immunogenicity, since the MTase is located in L protein, which is not a neutralizing antibody target. Thus, ablating viral mRNA cap methylation provides a new avenue to rationally attenuate these viruses for development of live attenuated vaccines.

SUMMARY OF THE INVENTION

The present invention provides recombinant paramyxovirus compositions comprising a nucleic acid molecule which encodes a defective mRNA cap MTase in a paramyxovirus viral genome. Provided are those compositions wherein the composition is defective in mRNA cap MTase gene expression. Also provided are those compositions wherein paramyxovirus viral genome is selected from the group consisting of: a human metapneumovirus (hMPV); human respiratory syncytial virus (hRSV); and human parainfluenza virus type 3 (PIV3).

The present invention also provides compositions wherein the nucleic acid molecule which encodes a defective mRNA cap MTase carries at least one mutation in the MTase catalytic site. Also provided are those compositions wherein the at least one mutation in the MTase catalytic site is in at least one of the K-D-K-E tetrad sites. Also provided are those compositions wherein the paramyxovirus is human metapneumovirus (hMPV) and the at least one K-D-K-E tetrad site mutation is at least one of rhMPV-K1673A, rhMPV-D1779A, rhMPV-K1817A, rhMPV-E1848A, and rhMPV-E1848Q. Also provided are those compositions wherein the paramyxovirus is human respiratory syncytial virus (hRSV) and the at least one K-D-K-E tetrad site mutation is at least one of rRSV-K1831A, rRSV-D1936A, rRSV-K1973A, rRSV-E2004A. Also provided are those compositions wherein the paramyxovirus is human parainfluenza virus type 3 (PIV3) and the at least one K-D-K-E tetrad site mutation is at least one of rPIV3-K1786A, rPIV3-D1905A, rPIV3-K1941A, rPIV3-E1978A.

The present invention also provides compositions wherein the nucleic acid molecule which encodes a defective mRNA cap MTase carries at least one mutation in the SAM binding site. Also provided are those compositions according to claim 9, wherein the at least one mutation in the SAM binding site is in the G×G×G . . . D/E/W site. Also provided are those compositions wherein the paramyxovirus is human metapneumovirus (hMPV) and the at least one mutation in the G×G×G . . . D/E/W site is at least one of rhMPV-G1696A, rhMPV-G1698A, rhMPV-G1700A, and rhMPV-D1755A. Also provided are those compositions wherein the paramyxovirus is human respiratory syncytial virus (hRSV) and the at least one mutation in the G×G×G . . . D/E/W site is at least one of rRSV-G1853A, rRSV-G1855A, rRSV-G1857A, and rRSV-D1912A. Also provided are those compositions wherein the paramyxovirus is human parainfluenza virus type 3 (PIV3) and the at least one mutation in the G×G×G . . . D/E/W site is at least one of rPIV3-G1808A, rPIV3-G1810A, rPIV3-G1812A, and rPIV3-W1880A. Also provided are those compositions wherein the nucleic acid molecule which encodes a defective mRNA cap MTase carries at least one mutation in the MTase catalytic site and the SAM binding site.

The present invention also provides compositions wherein the at least one mutation in the MTase catalytic site is in at least one of the K-D-K-E tetrad sites and the at least one mutation in the SAM binding site is in the G×G×G . . . D/E/W site. Also provided are those compositions wherein the paramyxovirus is human metapneumovirus (hMPV) and the at least one K-D-K-E tetrad site mutation is at least one of rhMPV-K1673A, rhMPV-D1779A, rhMPV-K1817A, rhMPV-E1848A, and rhMPV-E1848Q and the at least one mutation in the G×G×G . . . D/E/W site is at least one of rhMPV-G1696A, rhMPV-G1698A, rhMPV-G1700A, and rhMPV-D1755A. Also provided are those compositions wherein the paramyxovirus is human respiratory syncytial virus (hRSV) and the at least one K-D-K-E tetrad site mutation is at least one of rRSV-K1831A, rRSV-D1936A, rRSV-K1973A, rRSV-E2004A and the at least one mutation in the G×G×G . . . D/E/W site is at least one of rRSV-G1853A, rRSV-G1855A, rRSV-G1857A, and rRSV-D1912A. Also provided are those compositions wherein the paramyxovirus is human parainfluenza virus type 3 (PIV3) and the at least one K-D-K-E tetrad site mutation is at least one of rPIV3-K1786A, rPIV3-D1905A, rPIV3-K1941A, rPIV3-E1978A and the at least one mutation in the G×G×G . . . D/E/W site is at least one of rPIV3-G1808A, rPIV3-G1810A, rPIV3-G1812A, and rPIV3-W1880A.

Also provided are those compositions which are mammalian immunogens.

Also provided are those compositions which are human immunogens.

Also provided are methods of eliciting an immune response in a mammal comprising administering to a mammal a recombinant paramyxovirus composition herein. Also provided are methods wherein the composition is administered orally. Also provided are those compositions wherein the composition is administered intranasally.

Also provided are methods of preparing a pharmaceutical composition for passive immunization of an individual in need of immunization comprising mixing a paramyxovirus composition herein with a suitable excipient or carrier, thereby forming a pharmaceutical composition. Also provided are pharmaceutical compositions formulated for oral administration. Also provided are compositions wherein the pharmaceutical composition is formulated for intranasal administration. Also provided are pharmaceutical compositions wherein the paramyxovirus virulence is attenuated or eliminated in any mammal susceptible to paramyxovirus.

BRIEF DESCRIPTIONS OF THE FIGURES

The patent or application file contains at least one drawing executed in color and/or one or more photographs. Copies of this patent or patent application publication with color drawing(s) and/or photograph(s) will be provided by the Patent Office upon request and payment of the necessary fee. FIG. 1. Sequence alignment of conserved domain VI of L proteins of human paramyxoviruses and modeling with two known 2'-O MTase structures, VP39 (SEQ ID NO: 11) and RRMJ (SEQ ID NO: 10).

STR: structure of RRMJ and VP39. Predicted or known alpha-helical regions are shown as cylinders and the β-sheet regions as arrows. The conserved motifs (X and I to VIII) correspond to the SAM-dependent MTase superfamily are indicated. The predicted MTase active site (K-D-K-E tetrad) is shown by yellow boxes. The predicted SAM binding site (G×G×G - - - D/E/W) is shown by grey boxes. The conserved aromatic amino acid resides are shown by red boxes. Representative members of Paramyxoviridae (HMPV, human metapneumovirus (SEQ ID NO: 1); AMPVC, avian metapneumovirus type C (SEQ ID NO: 2); HRSV, human respiratory syncytial virus (SEQ ID NO: 3); BRSV, bovine respiratory syncytial virus (SEQ ID NO: 4); PVM, pneumonia virus of hamsters (SEQ ID NO: 5); PIV3, human parainfluenza virus type 3 (SEQ ID NO: 6); NDV, Newcastle disease virus (SEQ ID NO: 7)), Filoviridae (EBOM, Ebola virus (SEQ ID NO: 8)), Rhabdoviridae (VSIV, vesicular stomatitis virus Indiana serotype (SEQ ID NO: 9)) are shown.

Figure 2:
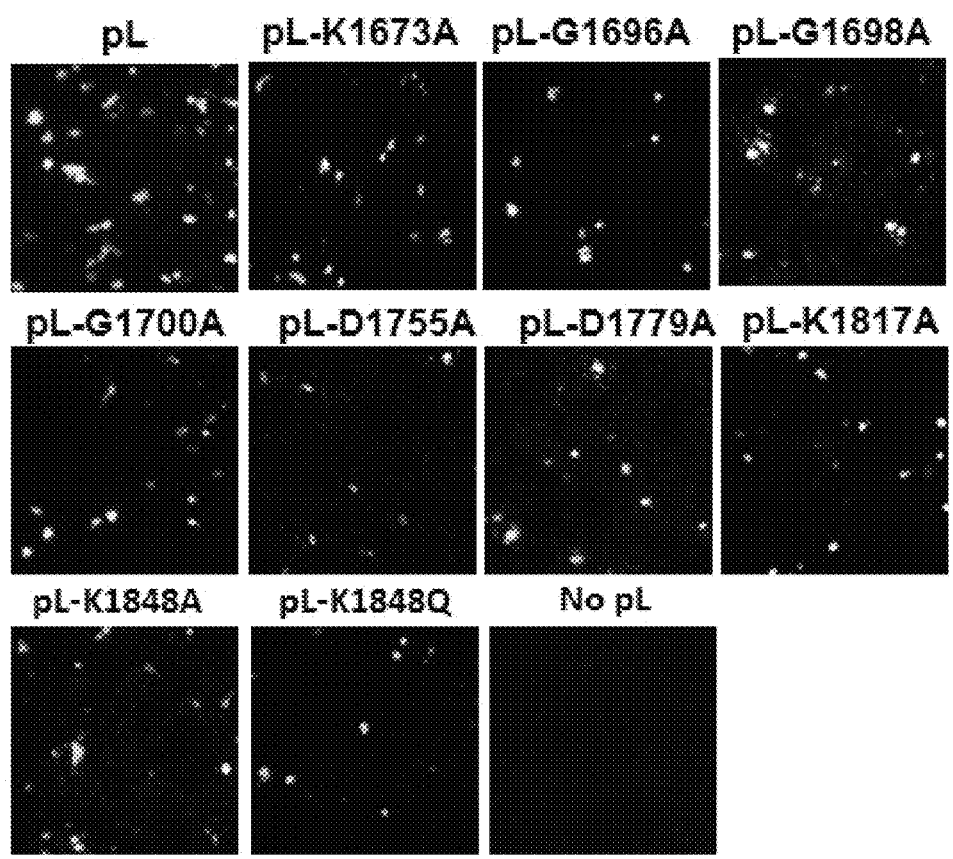

FIG. 2. Examination of the function of hMPV L protein by a minigenome assay.

A minigenome system was established to analyze the function of L protein carrying mutations in catalytic site or SAM binding site. To establish this system, the full-length genomic cDNA of hMPV in the plasmid (phMPV) was replaced by green fluorescent protein (GFP) flanked hMPV trailer and gene end sequences on one side and hMPV gene start and leader sequences on the other side, followed by the HDV ribozyme, and a T7 terminator, to yield phMPV-GFP. To achieve maximum level of minigenome replication, vaccinia vTF-7 was used as the source of T7 polymerase. Briefly, BHK cells were infected by vaccinia vTF-7 at a MOI of 10, followed by transfection of phMPV-GFP together with support plasmids (pN, pP, pL and pM2-1) using a standard protocol recommended by Invitrogen. Two days later, GFP expression was observed by fluorescence microscopy. Each amino acid residue in the MTase catalytic site and SAM binding site was substituted into alanine in the L gene of hMPV (pL) by site-directed mutagenesis. All plasmids were sequenced to confirm the presence of the designed mutation. The effect of each L gene mutation on GFP expression was analyzed by the minigenome assay as described above.

Figure 3:
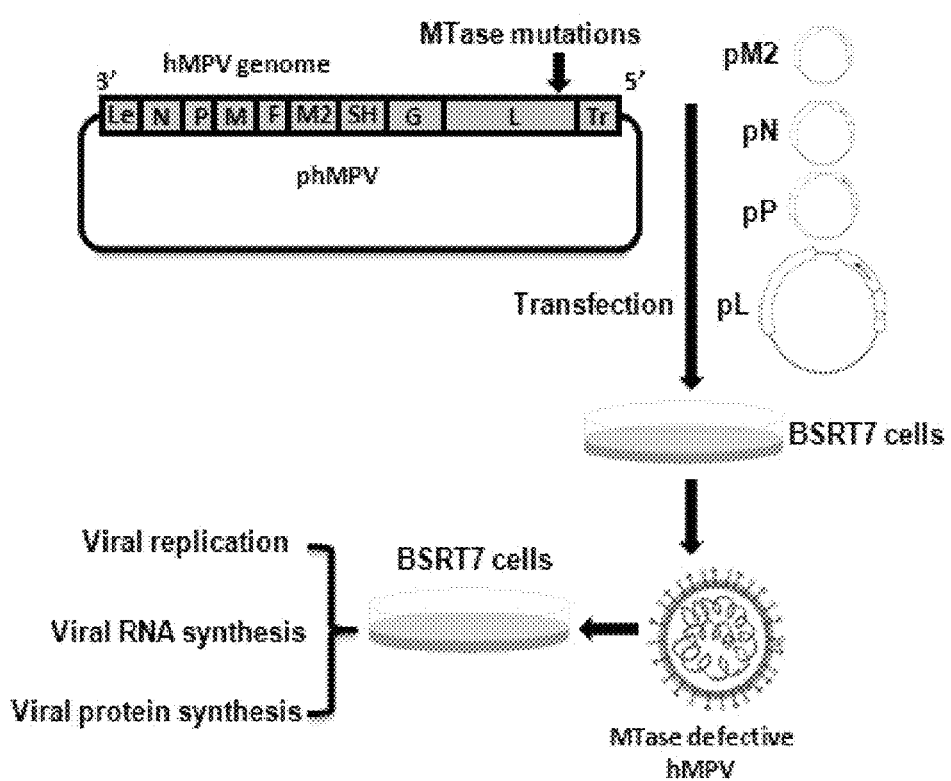

FIG. 3. Recovery of recombinant hMPV from full-length genomic cDNA clones.

A schematic hMPV genome comprising a leader region (Le); eight genes that encode the viral N, P, M, F, M2, SH, G and L proteins, and a trailer region (Tr), is shown. Recombinant hMPV was recovered by transfection of plasmids encoding the full-length hMPV genome (phMPV), pM2, pL, pP, and pN into BSRT7 cells which stably expressing T7 RNA polymerase. Six days post transfection, the cells were subjected to three freeze-thaw steps and the supernatant was used to infect Vero-E6 cells (ATCC). TPCK-typsin (0.5 μg/ml) was added to cells at day 2 post-infection since hMPV requires typsin to grow. Cytopathic effects (CPE) were observed after 5 day post-infection. Viruses were further amplified in Vero-E6 cells. Each amino acid residue in the MTase catalytic site and SAM binding site was substituted into alanine in the L gene of hMPV genome by site-directed mutagenesis. All plasmids were sequenced to confirm the presence of the designed mutation. Recombinant hMPVs carrying mutations in MTase catalytic and SAM binding site were recovered by an identical procedure as described above. Vero E6 cells were infected by the recovered hMPV and viral replication and protein synthesis was determined.

FIG. 4: Summary of recombinant viruses carrying mutations in either MTase catalytic site or SAM binding site.

Recombinant hMPV, RSV and PIV3 carrying mutations in either MTase catalytic site or SAM binding site were recovered by the procedure described in FIG. 2. Viral RNA was extracted from each recombinant virus. The entire L gene of each recombinant virus was amplified by reverse transcription-PCR (RT-PCR), and sequence analysis confirmed the presence of the desired mutation.

Figure 5:
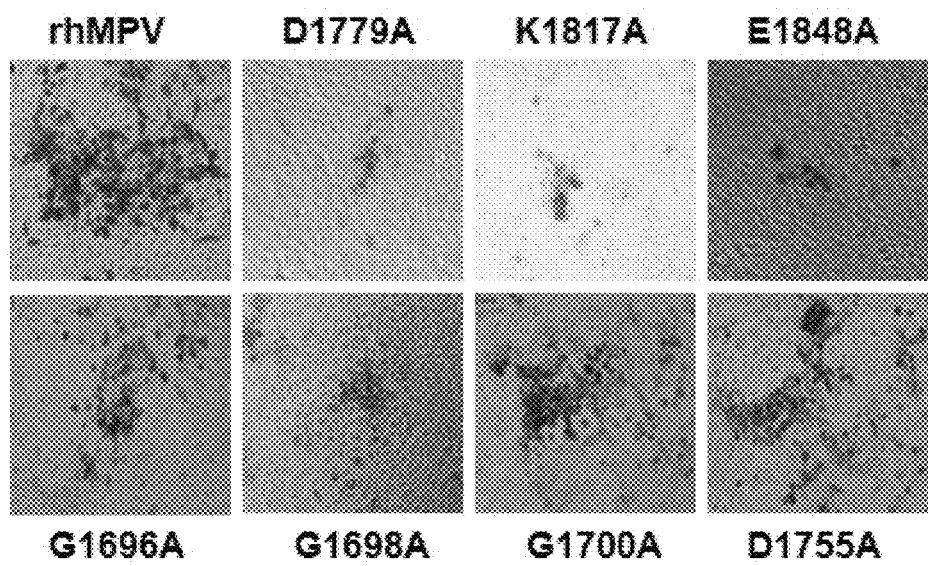

FIG. 5: Characterization of recombinant MTase-defective hMPV by immunostaining.

Recombinant hMPV forms plaques visualized by immunostaining. Vero E6 cells were infected with the indicated virus and overlayed with 2% methyl cellulose. After 5 days, the methyl cellulose was removed, and cells were incubated with a monoclonal antibody against hMPV N protein (Santa Cruz Biotechnology, Inc.), followed by incubation with horseradish peroxidase-labeled rabbit anti-guinea pig antibodies (Invitrogen). After incubation with AEC substrate chromogen (Invitrogen), viral plaques were visualized under the microscope.

Figure 6:
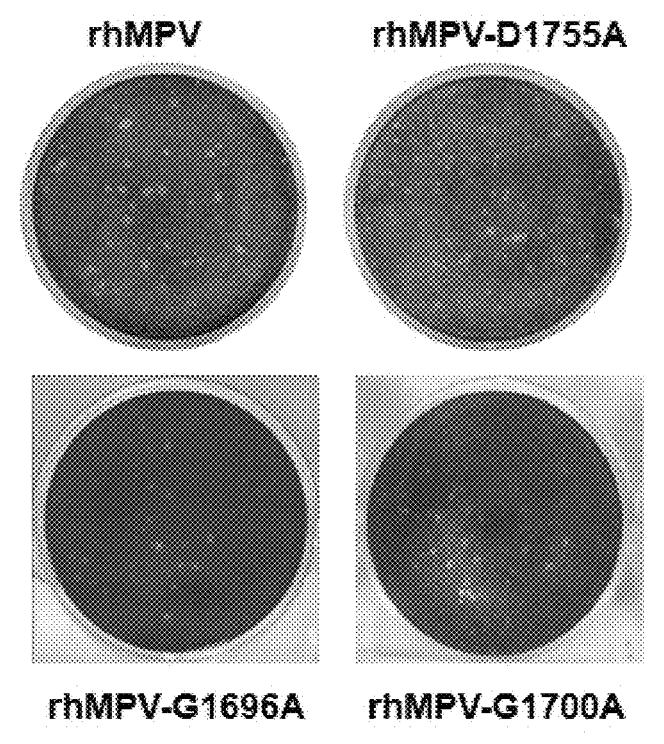

FIG. 6: Characterization of recombinant MTase-defective hMPV by agarose overlay plaque assay.

Recombinant hMPV forms small rounded plaques visualized by crystal violet staining. Vero-E6 cells were infected with indicated virus. After 1 h infection, the cells were overlaid with 2 ml of cell culture medium containing 0.5% agarose and 5% FBS, and incubated for 6 days. The plates were fixed by 10% formaldehyde, followed by staining the crystal violet.

Figure 7:
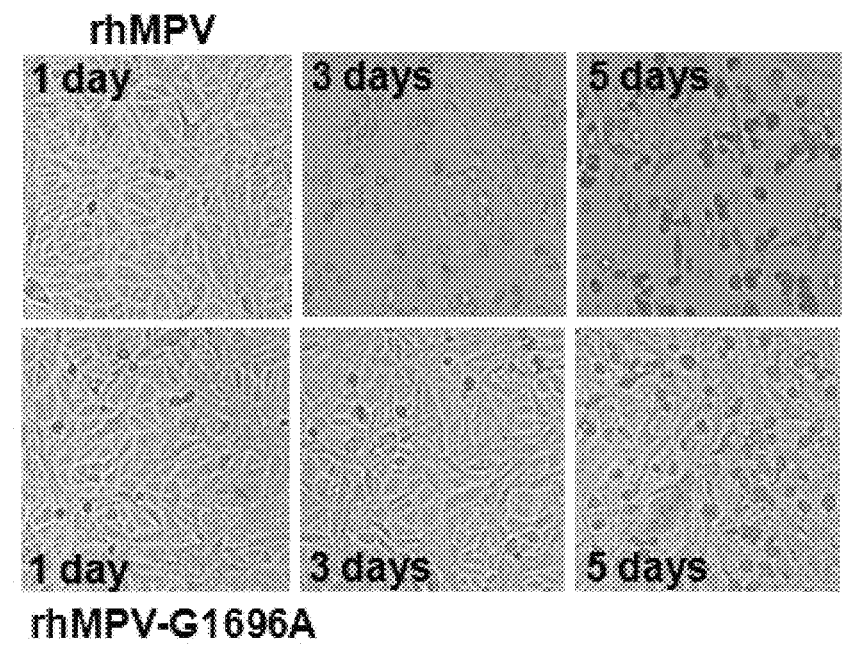

FIG. 7: MTase-defective recombinant hMPV has a delayed cytopathic effect (CPE) in Vero cells.

Recombinant MTase-defective rhMPV-G1696A was shown as an example. Vero E6 cells were infected with wild type rhMPV or rhMPV-G1696A at a MOI of 1, and the cytopathic effect (CPE) was observed at day 0, 3 and 5 post-infection by light microscopy.

Figure 8:
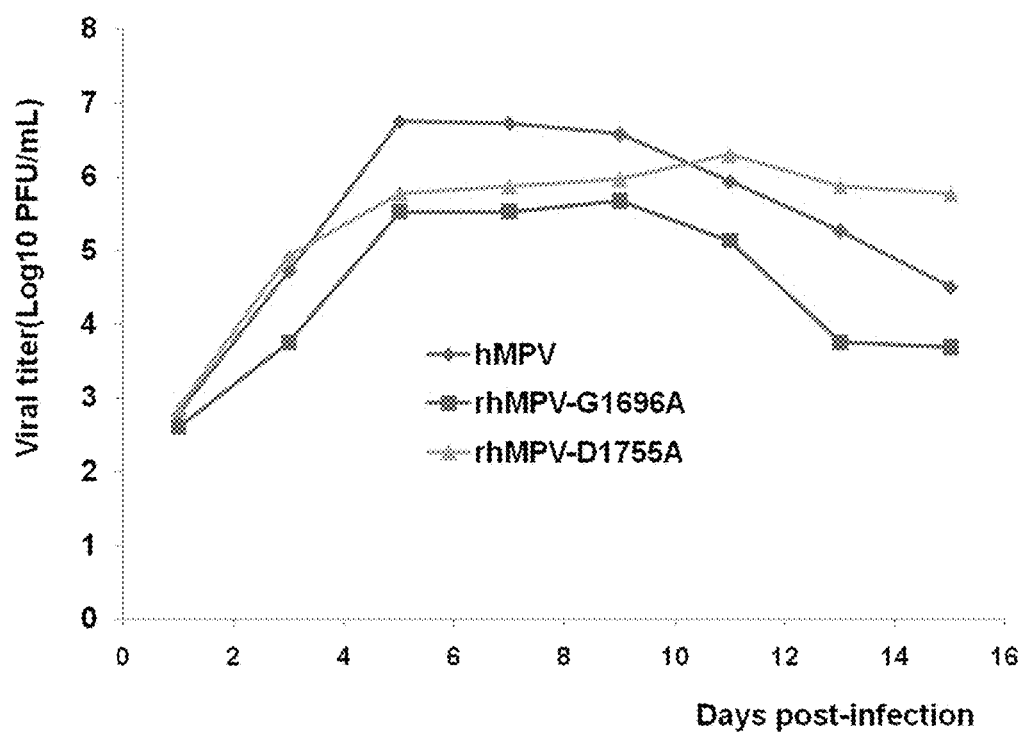

FIG. 8: Single step growth curves of MTase-defective rhMPV.

Confluent Vero E6 cells were infected with individual viruses at an MOI of 1. After 1 h of incubation, the inoculum was removed, the cells were washed with DMEM, and fresh medium (containing 2% fetal bovine serum) was added, followed by incubation at 37° C. Samples of supernatant were harvested at the indicated intervals over a 48-h time period, and the virus titer was determined by plaque assay using immunostaining. Titers are the average of three independent experiments.

Figure 9:
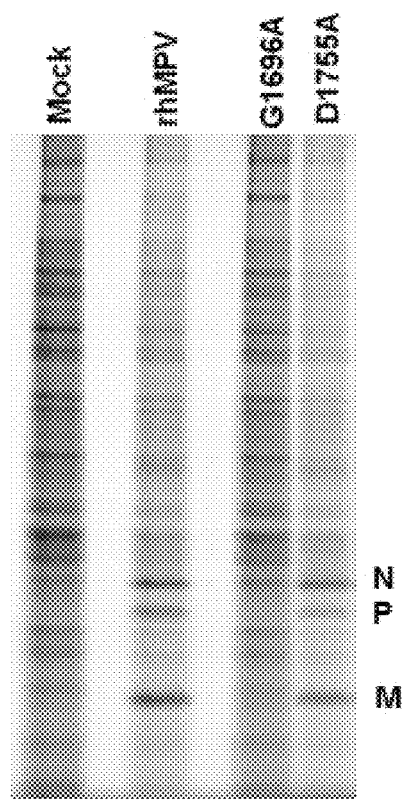

FIG. 9. Analysis of viral protein synthesis in virus-infected cells.

Confluent Vero E6 cells were infected with either rhMPV or MTase-defective rhMPV at a MOI of 1. After 48 h postinfection, cells were washed with methionine- and cysteine-free (M$^-$C$^-$) medium and incubated with fresh M$^-$C$^-$ medium supplemented with actinomycin D (15 μg/ml). After 1 h of incubation, the medium was replaced with M$^-$C$^-$ medium supplemented with EasyTag $^{35}$S-Express (4 μCi/ml; Perkin-Elmer, Wellesley, Mass.). After 24 h of incubation, cytoplasmic extracts were prepared and analyzed by sodium dodecyl sulfate-polyacrylamide gel electrophoresis (SDS-PAGE) as described previously. Labeled proteins were detected either by autoradiography or by using a phosphorimager.

FIG. 10A-FIG. 10B. Pathogenicity of MTase-defective hMPV in a hamster model (A) Diagram of proposed animal experiments. (B) Two-week-old female hamsters (Charles River laboratories, Wilmington, Mass.) were inoculated intranasally with three different doses ($6.48 \times 10^6$, $1.0 \times 10^5$, $1.0 \times 10^4$ PFU) of the wild type hMPV or MTase-defective hMPV. In one group, hamsters were inoculated with cell culture medium (DMEM) and served as uninfected controls. After inoculation, the animals were evaluated on a daily basis for mortality, weight loss, and the presence of any respiratory symptoms of hMPV. At day 4 post-infection, five hamsters from each group were sacrificed, and their lungs and nasal turbinates were removed for pathogenicity studies as follows. (i) Virus titer in lung. One lung from each animal was weighed and homologized in 1 ml of phosphate-buffered saline (PBS). Viral titer was determined by plaque assay and viral RNA was quantified by real-time reverse-transcriptase polymerase chain reaction (RT-PCR). (ii) Virus titer in nasal turbinate. Nasal turbinate from each hamster was removed, weighed, and virus titer was determined by plaque assay. (iii) Pulmonary histopathology. One lung from each hamster was inflated with 10% buffered formalin, embedded in paraffin, sectioned, and stained with hematoxylin-eosin. Histopathological changes were scored include the extent of inflammation (focal or diffuse), the pattern of inflammation (peribronchilolar, perivascular, interstitial, alveolar), and the nature of the cells making up the infiltrate (neutrophils, eosinophils, lymphocytes, macrophages). Deparaffinized sections were also stained with polyclonal antiserum to determine the distribution of viral antigen. Five animals per cohort was used in these experiments.

FIG. 11. Immunogenicity of MTase-defective hMPV in a hamster model

Two-week-old female hamsters were inoculated intranasally with two different doses ($10^5$ and $10^4$ PFU) of the MTase-defective hMPV strains. As the controls, hamsters were inoculated with PBS. Serum samples were collected at days 7, 14, 21, and 28 post-inoculation for the detection of humoral immune response. At day 28 post-inoculation, hamsters were sacrificed, and spleen samples were isolated for the detection of cellular immune response. The hamsters were also challenged with $10^6$ PFU of the wild-type hMPV. After the challenge, each animal was evaluated on a daily basis for weight loss and the presence of any respiratory symptoms. At day 4 post-challenge, all the animals were sacrificed and lung samples were collected for virus detection and pathological examination. The immunogenicity of the MTase-defective hMPV was evaluated as the following: (i) humoral immunity was determined by virus-serum neutralization assay using an end-point dilution plaque reduction assay. (ii) Cellular immunity was determined by a T cell proliferation assay. (iii) Viral clearance in the lungs. Lung samples were homogenized in PBS. Viral titer was determined by plaque assay and viral RNA was quantified by real-time RT-PCR. (iv) Evaluation of the protection efficacy after challenge. The protection was evaluated with respect to weight loss, respiratory symptoms, and pulmonary histopathology as described above.

DETAILED DESCRIPTION

The present invention provides methyltransferase (MTase)-defective recombinant viruses as live vaccine candidates for hMPV, RSV and PIV3. Messenger RNA (mRNA) modification is the essential issue in paramyxovirus gene expression and replication. During viral RNA synthesis, paramyxoviruses produce capped, methylated, and polyadenylated mRNAs. Methylation of the mRNA directly impacts the subsequent translation of viral proteins, which in turn affects viral genome replication, virus assembly, and budding. Viruses lacking MTase would likely be attenuated without affecting immunogenicity, since the MTase is located in L protein, which is not a neutralizing antibody target. Therefore, MTase is a novel and new target for the development of a stable and efficacious live vaccine. It is known that viral large RNA polymerase (L) protein of paramyxovirus contains mRNA cap MTase activity. L protein is a 230-250-KDa multifunctional protein consisting of 2005-2200 amino acids. Amino acid sequence alignments of the L protein of paramyxoviruses identified six conserved domains numbered I to VI. The MTase activity is located in the conserved domain VI of the L protein. Using a reverse genetics system, the inventors have successfully generated a panel of recombinant hMPV, RSV and PIV3 that are defective in MTase. These recombinant viruses were attenuated in cell culture as well as in hamster models. More importantly, these attenuated viruses elicited high level of neutralizing antibody and cellular immune response in hamsters, and protected hamsters from challenge of virulent viruses. Taken together, these MTase-defective viruses are excellent candidates for live attenuated vaccine for RSV, hMPV and PIV3.

MTase-Defective Viruses as Live Vaccine Candidates for hMPV.

Specifically, provided are MTase-defective hMPV carrying mutations in MTase catalytic site (rhMPV-K1673A, rhMPV-D1779A, rhMPV-K1817A, rhMPV-E1848A,) and SAM binding site (rhMPV-G1696A, rhMPV-G1698A, rhMPV-G1700A, and rhMPV-D1755A). All MTase-defective hMPV were attenuated in cell culture as well as in animal, and remained excellent immunogenicity. Therefore, MTase-defective hMPVs are excellent live vaccine candidates.

MTase-Defective Viruses as Live Vaccine Candidates for RSV.

Specifically, provided are MTase-defective RSV carrying mutations in MTase catalytic site (rRSV-K1831A, rRSV-D1936A, rRSV-K1973A, rRSV-E2004A,) and SAM binding site (rRSV-G1853A, rRSV-G1855A, rRSV-G1857A, and rRSV-D1912A). All MTase-defective RSV were attenuated in cell culture as well as in animal, and remained excellent immunogenicity. Therefore, MTase-defective RSVs are excellent live vaccine candidates. The virus strains that have been deposited with the American Type Culture Collection (ATCC) located at 10801 University Boulevard, Manassas, Va. 20110-2209 under the Accession Numbers: rRSV-G1853A having ATCC Accession NO: PTA-122916, deposited on Mar. 10, 2016; and, rRSV-G1857A having ATCC Accession NO: PTA-122915, deposited on Mar. 10, 2016; in accordance with the provisions of the Budapest Treaty, or any descendant or progeny of one of the aforementioned strains.

MTase-Defective Viruses as Live Vaccine Candidates for PIV3.

Specifically, provided are MTase-defective PIV3 carrying mutations in MTase catalytic site (rPIV3-K1786A, rPIV3-D1905A, rPIV3-K1941A, rPIV3-E1978A,) and SAM binding site (rPIV3-G1808A, rPIV3-G1810A, rPIV3-G1812A, and rPIV3-W1880A). All MTase-defective PIV3 were attenuated in cell culture as well as in animal, and remained excellent immunogenicity. Therefore, all MTase-defective PIV3 are excellent live vaccine candidates.

EXAMPLES

Example 1

Identification of Critical Amino Acid Residues that are Essential for mRNA Cap MTase To develop MTase-defective hMPV as live vaccine candidates, the inventors characterized critical amino acid residues that are essential for mRNA cap MTase. The SAM-dependent MTase superfamily contains six motifs involved in either SAM binding (motifs I, III, IV) or in the catalytic reaction (motifs IV, VI, VIII, X) (FIG. 1). Sequence alignment and structural modeling with crystal structure-solved ribose 2'-O MTases, vaccinia virus VP39 and *E. coli* RRMJ, identified these motifs in the conserved domain VI of paramyxovirus L proteins.

1.1. Putative catalytic site of the hMPV MTases. The SAM-dependent MTase superfamily contains a K-D-K-E tetrad that functions as the catalytic residues of the MTase. Structural modeling and amino acid sequence alignments indicate that residues K1673, D1779, K1817, and E1848 of the hMPV L protein correspond to the catalytic K-D-K-E tetrad (FIG. 1). In RSV, these amino acids are K1831, D1936, K1973, and E2004 (FIG. 1). In PIV3, these amino acids are K1786, D1905, K1941, and E1978 (FIG. 1).

1.2. Putative SAM binding site of the hMPV MTases. In methylation reactions, a G-rich motif and an acidic residue (D/E/W) are involved in binding the methyl donor, SAM. Indeed, this GxGxG . . . D/E/W motif is conserved in all paramyxoviruses. Sequence alignments indicate that the SAM binding site residues of hMPV L protein include G1696, G1698, G1700 and D1755 (FIG. 1). In RSV these amino acids are G1853, G1855, G1857, and D1912 (FIG. 1). In PIV3, these amino acids are G1808, G1810, G1812, and W1880 (FIG. 1).

Example 2

Examination of the Effect of Mutations to Catalytic Site and SAM Binding Site on Gene Expression by a Minigenome System The inventors used the minigenome assay to determine whether L protein is functional in replication and RNA synthesis in cells. If a mutant L is functional in the minigenome assay, the inventors may be able to recover recombinant hMPV carrying this mutation by reverse genetics. Briefly, a minigenome plasmid phMPV-GFP containing green fluorescent protein (GFP) flanked hMPV trailer and gene end sequences on one side and hMPV gene start and leader sequences on the other side was constructed. BHK cells were infected by vaccinia vTF-7 at a MOI of 10, followed by transfection of phMPV-GFP together with support plasmids expressing hMPV proteins (pN, pP, pL and pM2-1). Two days later, GFP expression was observed by fluorescence microscopy. As shown in FIG. 2, a strong GFP signal was observed when minigenome was transfected with wild type hMPV L (pL). As a negative control, no GFP expression was observed when pL was omitted from transfection. However, mutations in MTase catalytic site (pL-K1673A, pL-D1779A, pL-K1817A, and pL-E1848A) and SAM binding site (pL-G1696A, pL-G1698A, pL-G1700A, and pL-D1755A) had a diminished GFP expression level. This result demonstrated that mutations in catalytic site and SAM binding site of hMPV L protein were functional but had a diminished replication and/or gene expression. This result also suggests that we may be able to recover viable recombinant hMPV carrying these mutations since they are not lethal in replication and gene expression.

Example 3

Recovery of MTase-Defective Paramyxoviruses from Full-Length cDNA Clones

The inventors have successfully generated a panel of recombinant hMPV that are defective in mRNA cap MTase. The putative MTase catalytic K-D-K-E tetrad and potential SAM binding site GxGxG . . . D/E/W motif was individually mutated to alanine in the hMPV infectious clone. The mutations in MTase catalytic site were named K1673A, D1779A, K1817A, and E1848A. The mutations in SAM binding site were named G1696A, G1698A, G1700A and D1755A. Using the reverse genetics technique (FIG. 3), recombinant hMPV viruses carrying these mutations were recovered from an infectious cDNA clones. Briefly, recombinant hMPV was recovered by co-transfection of plasmid encoding full-length genomic cDNA of hMPV (phMPV) and support plasmids encoding viral N (pN), P (pP), L (pL) and M2-1 (pM2-1) proteins into BHK.SR19T7pac cells stably expressing T7 RNA polymerase. Six days post transfection, the cells were subjected to three freeze-thaw steps and the supernatant was used to infect Vero-E6 cells (ATCC). TPCK-typsin (0.5 μg/ml) was added to cells at day 2 post-infection since hMPV requires typsin to grow. Cytopathic effects (CPE) were observed after 5 day post-infection. Viruses were further amplified in Vero-E6 cells. Recombinant hMPV (rhMPV) carrying mutations in MTase catalytic site were named rhMPV-K1673A, rhMPV-D1779A, rhMPV-K1817A, and rhMPV-E1848A. Recombinant hMPV carrying mutations in SAM binding site were named rhMPV-G1696A, rhMPV-G1698A, rhMPV-G1700A and rhMPV-D1755A. All recombinant viruses were sequenced to confirm the presence of the designated amino acid changes in the L gene. These recombinant MTase-defective hMPVs were summarized in FIG. 4.

Using similar approaches, the inventors recovered a panel of MTase-defective RSV. Specifically, these MTase-defective RSVs carrying mutations in MTase catalytic site (rRSV-K1831A, rRSV-D1936A, rRSV-K1973A, rRSV-E2004A,) and SAM binding site (rRSV-G1853A, rRSV-G1855A, rRSV-G1857A, and rRSV-D1912A). All recombinant viruses were sequenced to confirm the presence of the designated amino acid changes in the L gene. These recombinant MTase-defective RSVs were summarized in FIG. 4.

Using similar approaches, the inventors recovered a panel of MTase-defective PIV3. Specifically, these MTase-defective PIV3 viruses carrying mutations in MTase catalytic site (rPIV3-K1786A, rPIV3-D1905A, rPIV3-K1941A, rPIV3-E1978A,) and SAM binding site (rPIV3-G1808A, rPIV3-G1810A, rPIV3-G1812A, and rPIV3-W1880A). All recombinant viruses were sequenced to confirm the presence of the designated amino acid changes in the L gene. These recombinant MTase-defective PIV3 were summarized in FIG. 4.

Example 4

MTase-Defective hMPVs were Attenuated in Cell Culture

The attenuation of MTase-defective hMPV in cell culture was determined by evaluation of the size of viral plaque, single-step virus growth curve, viral RNA synthesis, and viral protein synthesis. The inventors found that all the MTase-defective viruses carrying mutations either in MTase catalytic site (rhMPV-K1673A, rhMPV-D1779A, rhMPV-K1817A, and rhMPV-E1848A) or SAM binding site (rhMPV-G1696A, rhMPV-G1698A, rhMPV-G1700A and rhMPV-D1755A) were attenuated in cell culture. Specifically, all MTase-defective hMPV formed significantly smaller plaque size, had a delayed viral replication and single step growth curve, and had significantly less protein synthesis as compared to wild type hMPV.

FIG. 5 showed the viral plaque size by immunostaining assay. Briefly, Vero E6 cells were infected with the indicated virus and overlayed with 2% methyl cellulose. After 5 days, the methyl cellulose was removed, and cells were incubated with a monoclonal antibody against hMPV N protein (Santa Cruz Biotechnology, Inc.), followed by incubation with horseradish peroxidase-labeled rabbit anti-guinea pig antibodies (Invitrogen). After incubation with AEC substrate chromogen (Invitrogen), viral plaques were visualized under the microscope. As shown in FIG. 5, wild type hMPV formed big plaques after 5 days post-infection. However, recombinant MTase-defective hMPV formed significantly smaller plaques as compared to wild type hMPV. This result suggested that MTase-defective hMPV had a defect in cell-to-cell spread, replication or gene expression.

FIG. 6 showed viral plaque size by agarose overlay plaque assay. Briefly, Vero-E6 cells were infected with indicated virus. After 1 h infection, the cells were overlaid with 2 ml of cell culture medium containing 0.5% agarose and 5% FBS, and incubated for 6 days. The plates were fixed by 10% formaldehyde, followed by staining the crystal violet. As shown in FIG. 6, wild type hMPV forms rounded plaques visualized by crystal violet staining. However, MTase-defective hMPV formed smaller plaques as compared to wild type hMPV. Again, this data suggest that MTase-defective hMPV had a defect in cell-to-cell spread, replication or gene expression.

FIG. 7 showed cytopathic effect (CPE) of MTase-defective hMPV in Vero-E6 cells. Briefly, confluent Vero E6 cells were infected with individual viruses at an MOI of 1. CPE was monitored every day after infection. As shown in FIG. 7, wild type hMPV exhibited extensive CPE after 3 days post-infection and cells were killed at day 5 post-infection. However, MTase-defective hMPV had a significant delayed CPE. CPE was observed until day 8-10 days post-infection. Cells were not killed until day 14 post-infection. This results demonstrated MTase-defective hMPV had a defect in viral growth.

FIG. 8 showed a single-step growth curve of MTase-defective hMPV in cell culture. Briefly, confluent Vero E6 cells were infected with individual viruses at an MOI of 1. After 1 h of incubation, the inoculum was removed, the cells were washed with DMEM, and fresh medium (containing 2% fetal bovine serum) was added, followed by incubation at 37° C. Samples of supernatant were harvested at the indicated intervals over a 48-h time period, and the virus titer was determined by plaque assay using immunostaining. As shown in FIG. 8, wild type hMPV grew to high titer at 5 days post-infection and remained high titer after 5-10 days post-infection. After 10 days, virus titer gradually decreased. However, MTase-defective hMPV (rhMPV-G1696A and rhMPV-D1755A) had significant defects in viral growth curve. MTase-defective hMPV replicated to peak titer around 8-10 days post-infection and viral titer gradually decreased after 12 days post-infection. These results demonstrated that MTase-defective hMPV had significant defects in viral replication.

FIG. 9 showed viral protein synthesis of MTase-defective hMPV in Vero cells. Briefly, confluent Vero E6 cells were infected with either wild type rhMPV or MTase-defective rhMPV at a MOI of 1. After 48 h postinfection, cells were metabolically labeled with [35S] methionine. After 24 h of incubation, cytoplasmic extracts were prepared and analyzed by SDS-PAGE. Labeled proteins were detected by using a phosphorimager. As shown in FIG. 9, viral N, P and M proteins were detected in wild type hMPV. However, the abundance of viral proteins significantly diminished for MTase-defective hMPV. Only 20-30% and 60-70% of viral proteins were detected for recombinant rhMPV-G1696A and rhMPV-D1755A respectively. This result demonstrated that MTase-defective hMPV had defects in viral protein synthesis.

Taken together, MTase-defective hMPV was attenuated in cell culture as judged by viral plaque size, replication, growth curve and gene expression.

Example 5

MTase-Defective RSVs were Attenuated in Cell Culture

Using the techniques of the previous examples, the inventors found that certain MTase-defective RSVs carrying mutations in MTase catalytic site (rRSV-K1831A, rRSV-D1936A, rRSV-K1973A, rRSV-E2004A,) and SAM binding site (rRSV-G1853A, rRSV-G1855A, rRSV-G1857A, and rRSV-D1912A) were attenuated in cell culture.

Example 6

MTase-Defective PIV3s were Attenuated in Cell Culture

Using similar approaches, the inventors found that MTase-defective PIV3 viruses carrying mutations in MTase catalytic site (rPIV3-K1786A, rPIV3-D1905A, rPIV3-K1941A, rPIV3-E1978A,) and SAM binding site (rPIV3-G1808A, rPIV3-G1810A, rPIV3-G1812A, and rPIV3-W1880A) were attenuated in cell culture.

Example 7

Genetic Stability of MTase-Defective hMPV in Cell Culture

All MTase-defective were passed 10 times in Vero-E6 cells. At each passage, the L gene for each virus was sequenced to confirm the presence of the designed mutation. No additional mutation was found. These data indicated that MTase-defective hMPV is genetically stable in cell culture.

Example 8

MTase-Defective hMPV were Attenuated in Animal Models

To determine whether MTase-defective hMPVs are attenuated in animal, all recombinant viruses were inoculated into two-week-old specific-pathogen-free female hamsters (Charles River laboratories, Wilmington, Mass.). After inoculation, the animals were evaluated on a daily basis for mortality, weight loss, and the presence of any respiratory symptoms of hMPV. At day 4 post-infection, five hamsters from each group were sacrificed, and their lungs were removed for pathogenicity studies as follows. (i) Lung virus titer. One lung from each animal were weighed and homologized in 1 ml of phosphate-buffered saline (PBS). Viral titer was determined by plaque assay. (ii) Pulmonary histopathology. One lung from each hamster was inflated with 10% buffered formalin, embedded in paraffin, sectioned, and stained with hematoxylin-eosin. Histopathological changes were scored include the extent of inflammation (focal or diffuse), the pattern of inflammation (peribronchilolar, perivascular, interstitial, alveolar), and the nature of the cells making up the infiltrate (neutrophils, eosinophils, lymphocytes, macrophages). Deparaffinized sections were also stained with polyclonal antiserum to determine the distribution of viral antigen. Five animals per cohort were used in these experiments. The present results demonstrated that wild type hMPV was virulent to hamster (FIG. 10B). Specifically, hamsters inoculated with wild type hMPV exhibited mild clinical signs of respiratory tract infection, including ruffled fur, tendency to huddle, heavy breathing, and body weight losses. Wild type hMPV caused moderate to severe damage lung as confirmed by pulmonary histopathology. In contrast, all MTase-defective hMPV were highly attenuated in hamsters. Specifically, hamsters inoculated with MTase-defective hMPV did not exhibit any clinical sign for respiratory tract infection or weight loss. In addition, MTase-defective hMPV did not cause or only caused mild pulmonary histopathological changes (FIG. 10B). Taken together, these results demonstrated that MTase-defective hMPV were highly attenuated in hamsters and may be good live vaccine candidates for hMPV.

Example 9

MTase-Defective RSVs were Attenuated in Animal Models

Using similar approaches, the inventors found that MTase-defective RSVs carrying mutations in MTase catalytic site (rRSV-K1831A, rRSV-D1936A, rRSV-K1973A, rRSV-E2004A,) and SAM binding site (rRSV-G1853A, rRSV-G1855A, rRSV-G1857A, and rRSV-D1912A) were attenuated in animals.

Example 10

MTase-Defective PIV3s were Attenuated in Animal Models

Using similar approaches, the inventors found that MTase-defective PIV3 viruses carrying mutations in MTase catalytic site (rPIV3-K1786A, rPIV3-D1905A, rPIV3-K1941A, rPIV3-E1978A,) and SAM binding site (rPIV3-G1808A, rPIV3-G1810A, rPIV3-G1812A, and rPIV3-W1880A) were attenuated in animals.

Example 11

MTase-Defective hMPVs as Immunogens

To determine whether MTase-defective hMPV can be used as live vaccine candidates, the inventors examined the immunogenicity of these recombinant viruses. All MTase-defective hMPV were inoculated intranasally into two-week-old female hamsters (10 hamsters per group). Serum samples were collected at days 7, 14, 21, and 28 post-inoculation for the detection of humoral immune response. At day 28 post-inoculation, 5 hamsters from each group were sacrificed, and spleen samples were isolated for the detection of cellular immune response. The remaining 5 animals were challenged with $10^6$ PFU of the wild-type hMPV. After the challenge, each animal was evaluated on a daily basis for weight loss and the presence of any respiratory symptoms. At day 4 post-challenge, all the animals were sacrificed and lung samples were collected for virus detection and pathological examination. The immunogenicity of the MTase-defective hMPV was evaluated as the following: (i) humoral immunity was determined by virus-serum neutralization assay using an end-point dilution plaque reduction assay. (ii) Cellular immunity was determined by a T cell proliferation assay. (iii) Viral clearance in the lungs. Lung samples were homogenized in PBS. Viral titer was determined by plaque assay. (iv) Evaluation of the protection efficacy after challenge. The protection was evaluated with respect to weight loss, respiratory symptoms, and pulmonary histopathology as described above. The present results demonstrated that all MTase-defective hMPV elicited high level of neutralizing antibody and T cell immune response in hamsters, and protected hamsters from virulent challenge (FIG. 11). Specifically, severe lung damage was observed in PBS challenge control. However, no or only mild lung damage was observed in hamsters that were immunized by MTase-defective hMPV. Protection rate for each MTase-defective hMPV was 100%. These results demonstrated that MTase-defective hMPVs have excellent immunogenicity. Thus, MTase-defective hMPVs are excellent live vaccine candidates.

Example 12

MTase-Defective RSVs as Immunogens

Using similar approaches, the inventors found that MTase-defective RSVs carrying mutations in MTase catalytic site (rRSV-K1831A, rRSV-D1936A, rRSV-K1973A, rRSV-E2004A,) and SAM binding site (rRSV-G1853A, rRSV-G1855A, rRSV-G1857A, and rRSV-D1912A) retained excellent immunogenicity.

Example 13

MTase-Defective PIV3s as Immunogens

Using similar approaches, the inventors found that MTase-defective PIV3 viruses carrying mutations in MTase catalytic site (rPIV3-K1786A, rPIV3-D1905A, rPIV3-K1941A, rPIV3-E1978A,) and SAM binding site (rPIV3-G1808A, rPIV3-G1810A, rPIV3-G1812A, and rPIV3-W1880A) retained excellent immunogenicity.

What is claimed is:

1. A recombinant paramyxovirus composition comprising a nucleic acid molecule which encodes large RNA polymerase (L) protein having a defective mRNA cap MTase domain in a paramyxovirus viral genome, wherein the paramyxovirus viral genome is human respiratory syncytial virus (hRSV); and,
   wherein the nucleic acid molecule which encodes large RNA polymerase (L) protein having a defective mRNA cap MTase domain carries at least one mutation in a S-adenosyl methionine (SAM) binding site;
   wherein the at least one mutation in the SAM binding site is in a GxGxG . . . D/E/W site in an amino acid sequence corresponding to amino acid positions 31-90 of SEQ ID NO: 3, wherein the mutations comprise:
   at position 31, AxGxG . . . D;
   at position 33, GxAxG . . . D;
   at position 35, GxGxA . . . D; and,
   at position 90, GxGxG . . . A.

2. A method of eliciting an immune response in a human comprising: administering a recombinant paramyxovirus composition of claim 1.

3. The method of claim 2 wherein the composition is administered orally.

4. The method of claim 2 wherein the composition is administered intranasally.

5. A method of preparing an immunogenic composition comprising: mixing a paramyxovirus composition of claim 1 with a suitable excipient or carrier, thereby forming an immunogenic composition.

6. The method of claim 5 wherein the pharmaceutical composition is formulated for oral administration.

7. The method of claim 5 wherein the pharmaceutical composition is formulated for intranasal administration.

8. An isolated live human respiratory syncytial virus (hRSV) rRSV-G1853A, as deposited with American Type Culture Collection (ATCC) under the Accession Number PTA-122916.

9. An isolated live human respiratory syncytial virus (hRSV) rRSV-G1857A, as deposited with American Type Culture Collection (ATCC) under the Accession Number PTA-122915.

* * * * *

UNITED STATES PATENT AND TRADEMARK OFFICE
CERTIFICATE OF CORRECTION

PATENT NO. : 9,572,876 B2
APPLICATION NO. : 14/124501
DATED : February 21, 2017
INVENTOR(S) : Jianrong Li, Yu Zhang and Rongzhang Wang It is certified that error appears in the above-identified patent and that said Letters Patent is hereby corrected as shown below:

In the Specification

Column 1, Lines 16-19 replace the Government Support Clause with:
--This invention was made with government support under grant numbers AI090060 and RR025755 awarded by the National Institutes of Health. The government has certain rights in the invention.--

Signed and Sealed this
Sixth Day of October, 2020

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 194
<212> TYPE: PRT
<213> ORGANISM: Human metapneumovirus

<400> SEQUENCE: 1

Phe Val Phe Ser Ser Thr Gly Cys Lys Val Ser Leu Lys Thr Cys Ile
1               5                   10                  15
```

Gly Lys Leu Met Lys Asp Leu Asn Pro Lys Val Leu Tyr Phe Ile Gly
            20                  25                  30

Glu Gly Ala Gly Asn Trp Met Ala Arg Thr Ala Cys Glu Tyr Pro Asp
        35                  40                  45

Ile Lys Phe Val Tyr Arg Ser Leu Lys Asp Asp Leu Asp His His Tyr
 50                  55                  60

Pro Leu Glu Tyr Gln Arg Val Ile Gly Glu Leu Ser Arg Ile Ile Asp
 65                  70                  75                  80

Ser Gly Glu Gly Leu Ser Met Glu Thr Thr Asp Ala Thr Gln Lys Thr
                85                  90                  95

His Trp Asp Leu Ile His Arg Val Ser Lys Asp Ala Leu Leu Ile Thr
                100                 105                 110

Leu Cys Asp Ala Glu Phe Lys Asp Arg Asp Asp Phe Phe Lys Met Val
            115                 120                 125

Ile Leu Trp Arg Lys His Val Leu Ser Cys Arg Ile Cys Thr Thr Tyr
130                 135                 140

Gly Thr Asp Leu Tyr Leu Phe Ala Lys Tyr His Ala Lys Asp Cys Asn
145                 150                 155                 160

Val Lys Leu Pro Phe Val Arg Ser Val Ala Thr Phe Ile Met Gln
                165                 170                 175

Gly Ser Lys Leu Ser Gly Ser Glu Cys Tyr Ile Leu Leu Thr Leu Gly
            180                 185                 190

His His

<210> SEQ ID NO 2
<211> LENGTH: 194
<212> TYPE: PRT
<213> ORGANISM: Avian metapneumovirus

<400> SEQUENCE: 2

Phe Val Phe Ser Ser Thr Gly Cys Lys Ile Ser Val Lys Ala Cys Ile
 1               5                  10                  15

Gly Lys Leu Ile Gln Asp Leu Asn Pro Thr Val Phe Tyr Phe Val Gly
            20                  25                  30

Glu Gly Ala Gly Asn Trp Met Ala Arg Thr Ala Cys Glu Tyr Pro Asn
        35                  40                  45

Ala Lys Phe Val Tyr Arg Ser Leu Lys Asp Asp Leu Asp His His Phe
 50                  55                  60

Pro Leu Glu Phe Gln Arg Val Leu Gly Asn Met Asn Arg Val Ile Asp
 65                  70                  75                  80

Gly Gly Glu Gly Leu Ser Met Asp Thr Thr Asp Ala Thr Gln Lys Thr
                85                  90                  95

His Trp Asp Leu Ile His Arg Ile Cys Lys Asp Ala Leu Leu Ile Thr
                100                 105                 110

Leu Cys Asp Ala Glu Phe Lys Asp Arg Asp Asp Phe Phe Lys Met Val
            115                 120                 125

Thr Leu Trp Arg Lys His Val Leu Ser Cys Arg Ile Cys Thr Thr Tyr
130                 135                 140

Gly Thr Asp Leu Tyr Leu Phe Ala Lys Tyr His Ala Lys Glu Gln Ser
145                 150                 155                 160

Ile Lys Leu Pro Tyr Phe Val Arg Ser Ile Ala Thr Tyr Val Met Gln
                165                 170                 175

Gly Ser Lys Leu Ser Gly Ser Glu Cys Tyr Val Leu Leu Thr Leu Ser
            180                 185                 190

His His

<210> SEQ ID NO 3
<211> LENGTH: 192
<212> TYPE: PRT
<213> ORGANISM: Human respiratory syncytial virus

<400> SEQUENCE: 3

```
Phe Val Phe Ser Ser Thr Gly Cys Lys Ile Ser Ile Glu Tyr Ile Leu
1               5                   10                  15

Lys Asp Leu Lys Ile Lys Asp Pro Asn Cys Ile Ala Phe Ile Gly Glu
            20                  25                  30

Gly Ala Gly Asn Leu Leu Arg Thr Val Val Glu Leu His Pro Asp
        35                  40                  45

Ile Arg Tyr Ile Tyr Arg Ser Leu Lys Asp Cys Asn Asp His Ser Leu
    50                  55                  60

Pro Ile Glu Phe Leu Arg Leu Tyr Asn Gly His Ile Asn Ile Asp Tyr
65                  70                  75                  80

Gly Glu Asn Leu Thr Ile Pro Ala Thr Asp Ala Thr Asn Asn Ile His
                85                  90                  95

Trp Ser Tyr Leu His Ile Lys Phe Ala Glu Pro Ile Ser Leu Phe Val
            100                 105                 110

Cys Asp Ala Glu Leu Ser Val Thr Val Asn Trp Ser Lys Ile Ile Ile
        115                 120                 125

Glu Trp Ser Lys His Val Arg Lys Cys Lys Tyr Cys Ser Ser Val Asn
    130                 135                 140

Lys Cys Met Leu Ile Val Lys Tyr His Ala Gln Asp Asp Ile Asp Phe
145                 150                 155                 160

Lys Leu Asp Asn Ile Thr Ile Leu Lys Thr Tyr Val Cys Leu Gly Ser
                165                 170                 175

Lys Leu Lys Gly Ser Glu Val Tyr Leu Val Leu Thr Ile Gly Pro Ala
            180                 185                 190
```

<210> SEQ ID NO 4
<211> LENGTH: 192
<212> TYPE: PRT
<213> ORGANISM: Bovine respiratory syncytial virus

<400> SEQUENCE: 4

```
Phe Val Phe Ser Ser Thr Gly Cys Lys Ile Ser Thr Lys Leu Ile Leu
1               5                   10                  15

Lys Asp Leu Lys Ile Lys Asp Pro His Cys Ile Ala Phe Ile Gly Glu
            20                  25                  30

Gly Ala Gly Asn Leu Leu Leu Arg Thr Val Val Glu Leu His Pro Asp
        35                  40                  45

Ile Lys Tyr Ile Tyr Arg Ser Leu Lys Asp Cys Asn Asp His Ser Leu
    50                  55                  60

Pro Ile Glu Phe Leu Arg Leu Tyr Asn Gly His Ile Ser Ile Asp Tyr
65                  70                  75                  80

Gly Glu Asn Leu Thr Ile Pro Ala Thr Asp Ala Thr Asn Ala Ile His
                85                  90                  95

Trp Ser Tyr Leu His Ile Arg Tyr Ala Glu Pro Ile Asn Leu Phe Val
            100                 105                 110

Cys Asp Ala Glu Leu Pro Asp Leu Thr Asn Trp Ser Arg Ile Val Ser
        115                 120                 125
```

```
Glu Trp Tyr Lys His Val Arg Cys Cys Lys Tyr Cys Ser Thr Ile Asp
            130                 135                 140

Arg Ser Lys Leu Ile Val Lys Tyr His Ala Gln Asp Ile Thr Asp Phe
145                 150                 155                 160

Lys Leu Asn Asn Ile Ser Ile Val Lys Thr Tyr Val Cys Leu Gly Ser
                165                 170                 175

Lys Leu Lys Gly Ser Glu Val Tyr Leu Val Leu Thr Val Gly Pro Ser
            180                 185                 190

<210> SEQ ID NO 5
<211> LENGTH: 194
<212> TYPE: PRT
<213> ORGANISM: Pneumonia virus of hamsters

<400> SEQUENCE: 5

Phe Val Phe Ser Ser Thr Gly Cys Lys Val Ser Val Ile Asp Met Leu
1               5                   10                  15

Pro Lys His Phe Gln Arg Ser Asn Leu Lys Val Ile Cys Phe Ile Gly
            20                  25                  30

Glu Gly Ala Gly Asn Leu Met Leu Arg Ala Val Leu Glu Val Gly Gly
        35                  40                  45

Asn Ile Lys Leu Ile Tyr Arg Ser Leu Lys Asp Pro Asp Asp His His
50                  55                  60

Val Pro Val Glu Phe Leu Arg Leu Lys Pro Cys Tyr Pro Tyr Ile Asp
65                  70                  75                  80

Thr Gly Gly Ser Leu Ser Leu Ala Ser Thr Asp Ala Thr Asn Lys Ala
                85                  90                  95

His Trp Asp Tyr Leu His Leu His Trp Thr Asp Pro Leu Asn Leu Ile
            100                 105                 110

Val Cys Asp Ala Glu Ile Ser Gly Val Lys His Trp Leu Lys Ile Leu
        115                 120                 125

His Arg Trp Tyr Glu His Met Thr Ser Cys Lys His Cys Leu Lys Ser
130                 135                 140

Glu His Asp Lys Tyr Leu Ile Ile Lys Tyr His Ala Gln Asp Asp Leu
145                 150                 155                 160

Ile Asp Leu Pro His Gly Val Arg Leu Leu Lys Cys Asn Ile Cys Leu
                165                 170                 175

Gly Ser Lys Leu Ser Gly Ser Glu Ser Tyr Leu Leu Ile Gly Leu Gly
            180                 185                 190

Leu Ser

<210> SEQ ID NO 6
<211> LENGTH: 211
<212> TYPE: PRT
<213> ORGANISM: Human parainfluenza virus

<400> SEQUENCE: 6

Gly Ile Asn Ser Thr Ser Cys Leu Lys Ala Leu Glu Leu Ser Gln Ile
1               5                   10                  15

Leu Met Lys Glu Val Asn Lys Asp Gln Asp Arg Leu Phe Leu Gly Glu
            20                  25                  30

Gly Ala Gly Ala Met Leu Ala Cys Tyr Asp Ala Thr Leu Gly Pro Ala
        35                  40                  45

Val Asn Tyr Tyr Asn Ser Gly Leu Asn Ile Thr Asp Val Ile Gly Gln
50                  55                  60

Arg Glu Leu Lys Ile Phe Pro Ser Glu Val Ser Leu Val Gly Lys Lys
```

```
                65                  70                  75                  80
Leu Gly Asn Val Thr Gln Ile Leu Asn Arg Val Lys Val Leu Phe Asn
                    85                  90                  95

Gly Asn Pro Asn Ser Thr Trp Ile Gly Asn Met Glu Cys Glu Thr Leu
            100                 105                 110

Ile Trp Ser Glu Leu Asn Asp Lys Ser Ile Gly Leu Val His Cys Asp
            115                 120                 125

Met Glu Gly Ala Ile Gly Lys Ser Glu Thr Val Leu His Glu His
    130                 135                 140

Tyr Ser Val Ile Arg Ile Thr Tyr Leu Ile Gly Asp Asp Val Val
145                 150                 155                 160

Leu Ile Ser Lys Ile Ile Pro Thr Ile Thr Pro Asn Trp Ser Arg Ile
                165                 170                 175

Leu Tyr Leu Tyr Lys Leu Tyr Trp Lys Asp Val Ser Ile Ile Ser Leu
            180                 185                 190

Lys Thr Ser Asn Pro Ala Ser Thr Glu Leu Tyr Leu Ile Ser Lys Asp
            195                 200                 205

Ala Tyr Cys
    210

<210> SEQ ID NO 7
<211> LENGTH: 217
<212> TYPE: PRT
<213> ORGANISM: Newcastle disease virus

<400> SEQUENCE: 7

Gly Thr Ala Ser Ser Ser Trp Tyr Lys Ala Ser His Leu Leu Ser Val
1               5                   10                  15

Pro Glu Val Arg Cys Ala Arg His Gly Asn Ser Leu Tyr Leu Ala Glu
                20                  25                  30

Gly Ser Gly Ala Ile Met Ser Leu Leu Glu Leu His Val Pro His Glu
            35                  40                  45

Thr Ile Tyr Tyr Asn Thr Leu Phe Ser Asn Glu Met Asn Pro Pro Gln
    50                  55                  60

Arg His Phe Gly Pro Thr Pro Thr Gln Phe Leu Asn Ser Val Val Tyr
65                  70                  75                  80

Arg Asn Leu Gln Ala Glu Val Thr Cys Lys Asp Gly Phe Val Gln Glu
                85                  90                  95

Phe Arg Pro Leu Trp Arg Glu Asn Thr Glu Glu Ser Asp Leu Thr Ser
            100                 105                 110

Asp Lys Ala Val Gly Tyr Ile Thr Ser Ala Val Pro Tyr Arg Ser Val
            115                 120                 125

Ser Leu Leu His Cys Asp Ile Glu Ile Pro Pro Gly Ser Asn Gln Ser
        130                 135                 140

Leu Leu Asp Gln Leu Ala Ile Asn Leu Ser Leu Ile Ala Met His Ser
145                 150                 155                 160

Val Arg Glu Gly Gly Val Val Ile Ile Lys Val Leu Tyr Ala Met Gly
                165                 170                 175

Tyr Tyr Phe His Leu Leu Met Asn Leu Phe Ala Pro Cys Ser Thr Lys
            180                 185                 190

Gly Tyr Ile Leu Ser Asn Gly Tyr Ala Cys Arg Gly Asp Met Glu Cys
            195                 200                 205

Tyr Leu Val Phe Val Met Gly Tyr Leu
    210                 215
```

<210> SEQ ID NO 8
<211> LENGTH: 202
<212> TYPE: PRT
<213> ORGANISM: Ebola virus

<400> SEQUENCE: 8

```
Gly Ile Val Ser Ser Met His Tyr Lys Leu Asp Glu Val Leu Trp Glu
1               5                   10                  15

Ile Glu Ser Phe Lys Ser Ala Val Thr Leu Ala Glu Gly Glu Gly Ala
            20                  25                  30

Gly Ala Leu Leu Leu Ile Gln Lys Tyr Gln Val Lys Thr Leu Phe Phe
        35                  40                  45

Asn Thr Leu Ala Thr Glu Ser Ser Ile Glu Ser Glu Ile Val Ser Gly
    50                  55                  60

Met Thr Thr Pro Arg Met Leu Pro Val Met Ser Lys Phe His Asn
65                  70                  75                  80

Asp Gln Ile Glu Ile Ile Leu Asn Asn Ser Ala Ser Gln Ile Thr Asp
                85                  90                  95

Ile Thr Asn Pro Thr Trp Phe Lys Asp Gln Arg Ala Arg Leu Pro Lys
            100                 105                 110

Gln Val Glu Val Ile Thr Met Asp Ala Glu Thr Thr Glu Asn Ile Asn
        115                 120                 125

Arg Ser Lys Leu Tyr Glu Ala Val Tyr Lys Leu Ile Leu His His Ile
    130                 135                 140

Asp Pro Ser Val Leu Lys Ala Val Val Leu Lys Val Phe Leu Ser Asp
145                 150                 155                 160

Thr Glu Gly Met Leu Trp Leu Asn Asp Asn Leu Ala Pro Phe Phe Ala
                165                 170                 175

Thr Gly Tyr Leu Ile Lys Pro Ile Thr Ser Ser Ala Arg Ser Ser Glu
            180                 185                 190

Trp Tyr Leu Cys Leu Thr Asn Phe Leu Ser
        195                 200
```

<210> SEQ ID NO 9
<211> LENGTH: 201
<212> TYPE: PRT
<213> ORGANISM: Vesicular stomatitis virus

<400> SEQUENCE: 9

```
Gln Leu Pro Thr Gly Ala His Tyr Lys Ile Arg Ser Ile Leu His Gly
1               5                   10                  15

Met Gly Ile His Tyr Arg Asp Phe Leu Ser Cys Gly Asp Gly Ser Gly
            20                  25                  30

Gly Met Thr Ala Ala Leu Leu Arg Glu Asn Val His Ser Arg Gly Ile
        35                  40                  45

Phe Asn Ser Leu Leu Glu Leu Ser Gly Ser Val Met Arg Gly Ala Ser
    50                  55                  60

Pro Glu Pro Pro Ser Ala Leu Glu Thr Leu Gly Gly Asp Lys Ser Arg
65                  70                  75                  80

Cys Val Asn Gly Glu Thr Cys Trp Glu Tyr Pro Ser Asp Leu Cys Asp
                85                  90                  95

Pro Arg Thr Trp Asp Tyr Phe Leu Arg Leu Lys Ala Gly Leu Gly Leu
            100                 105                 110

Gln Ile Asp Leu Ile Val Met Asp Met Glu Val Arg Asp Ser Ser Thr
        115                 120                 125
```

-continued

```
Ser Leu Lys Ile Glu Thr Asn Val Arg Asn Tyr Val His Arg Ile Leu
    130                 135                 140

Asp Glu Gln Gly Val Leu Ile Tyr Lys Thr Tyr Gly Thr Tyr Ile Cys
145                 150                 155                 160

Glu Ser Glu Lys Asn Ala Val Thr Ile Leu Gly Pro Met Phe Lys Thr
                165                 170                 175

Val Asp Leu Val Gln Thr Glu Phe Ser Ser Ser Gln Thr Ser Glu Val
            180                 185                 190

Tyr Met Val Cys Lys Gly Leu Lys Lys
        195                 200

<210> SEQ ID NO 10
<211> LENGTH: 175
<212> TYPE: PRT
<213> ORGANISM: Escherichia coli

<400> SEQUENCE: 10

Gly Leu Arg Ser Arg Ala Trp Phe Lys Leu Asp Glu Ile Gln Gln Ser
1               5                   10                  15

Asp Lys Leu Phe Lys Pro Gly Met Thr Val Val Asp Leu Gly Ala Ala
            20                  25                  30

Pro Gly Gly Trp Ser Gln Tyr Val Gly Lys Gly Arg Ile Ile Ala Cys
        35                  40                  45

Asp Leu Leu Pro Met Asp Pro Ile Val Gly Val Asp Phe Leu Gln Gly
    50                  55                  60

Asp Phe Arg Asp Glu Leu Val Met Lys Ala Leu Leu Glu Arg Val Gly
65                  70                  75                  80

Asp Ser Lys Val Gln Val Val Met Ser Asp Met Ala Pro Asn Met Ser
                85                  90                  95

Gly Thr Pro Ala Val Asp Ile Pro Arg Ala Met Tyr Leu Val Glu Leu
            100                 105                 110

Ala Leu Glu Met Cys Arg Asp Val Leu Ala Pro Gly Gly Ser Phe Val
        115                 120                 125

Val Lys Val Phe Gln Gly Glu Gly Phe Asp Glu Tyr Leu Arg Glu Ile
    130                 135                 140

Arg Ser Leu Phe Thr Lys Val Lys Val Arg Lys Pro Asp Ser Ser Arg
145                 150                 155                 160

Ala Arg Ser Arg Glu Val Tyr Ile Val Ala Thr Gly Arg Lys Pro
                165                 170                 175

<210> SEQ ID NO 11
<211> LENGTH: 185
<212> TYPE: PRT
<213> ORGANISM: Vaccinia virus

<400> SEQUENCE: 11

Lys Leu Pro Tyr Gln Gly Gln Leu Lys Leu Leu Leu Gly Glu Leu Phe
1               5                   10                  15

Phe Leu Ser Lys Leu Gln Arg His Gly Ile Leu Asp Gly Ala Thr Val
            20                  25                  30

Val Tyr Ile Gly Ser Ala Pro Gly Thr His Ile Arg Tyr Leu Arg Asp
        35                  40                  45

His Phe Tyr Asn Leu Gly Met Ile Ile Lys Trp Met Leu Ile Asp Gly
    50                  55                  60

Arg His His Asp Pro Ile Leu Asn Gly Leu Arg Asp Val Thr Leu Val
65                  70                  75                  80
```

```
Thr Arg Phe Val Asp Glu Glu Tyr Leu Arg Ser Ile Lys Lys Gln Leu
            85              90              95

His Pro Ser Lys Ile Ile Leu Ile Ser Asp Val Arg Ser Lys Arg Gly
            100             105             110

Gly Asn Glu Pro Ser Thr Ala Asp Leu Leu Ser Asn Tyr Ala Leu Gln
            115             120             125

Asn Val Met Ile Ser Ile Leu Asn Pro Val Ala Ser Ser Leu Lys Trp
        130             135             140

Arg Cys Pro Phe Pro Asp Gln Trp Ile Lys Asp Phe Tyr Ile Pro His
145             150             155             160

Gly Asn Lys Met Leu Gln Pro Phe Ala Pro Ser Tyr Ser Ala Glu Met
                165             170             175

Arg Leu Leu Ser Ile Tyr Thr Gly Glu
            180             185
```